United States Patent
Rosenberg et al.

(10) Patent No.: US 6,215,470 B1
(45) Date of Patent: *Apr. 10, 2001

(54) USER INTERFACE DEVICE INCLUDING BRAKING MECHANISM FOR INTERFACING WITH COMPUTER SIMULATIONS

(76) Inventors: Louis B. Rosenberg, 849 Palomino Dr., Pleasanton, CA (US) 94566; Ramon Alarcon, 8-C Abrams Ct., Stanford, CA (US) 94305

( * ) Notice: Subject to any disclaimer, the term of this patent is extended or adjusted under 35 U.S.C. 154(b) by 0 days.

This patent is subject to a terminal disclaimer.

(21) Appl. No.: 09/153,938

(22) Filed: Sep. 16, 1998

Related U.S. Application Data

(63) Continuation of application No. 08/825,412, filed on Mar. 28, 1997, now Pat. No. 5,821,920, which is a continuation of application No. 08/344,148, filed on Nov. 23, 1994, now abandoned, which is a continuation of application No. 08/275,120, filed on Jul. 14, 1994, now Pat. No. 5,623,582.

(51) Int. Cl.[7] .................................................... G06F 3/033
(52) U.S. Cl. .............................................................. 345/156
(58) Field of Search .................................... 345/156–158, 345/161, 165, 166, 184; 318/567–568.11; 604/264; 434/45, 262, 267, 272

(56) References Cited

U.S. PATENT DOCUMENTS

| | | | |
|---|---|---|---|
| 2,906,179 | 9/1959 | Bower | 90/13.5 |
| 3,890,958 | 6/1975 | Fister et al. | 128/2 S |
| 3,919,691 | 11/1975 | Noll | 340/172.5 |
| 3,944,798 | 3/1976 | Eaton | 235/151.3 |
| 4,216,467 | 8/1980 | Colston | 340/365 |
| 4,391,282 | 7/1983 | Ando et al. | 128/660 |
| 4,398,889 | 8/1983 | Lam et al. | 434/45 |

(List continued on next page.)

FOREIGN PATENT DOCUMENTS

| | | |
|---|---|---|
| 0 085 518 A1 | 8/1983 | (EP) . |
| 2254911A | 10/1992 | (GB) . |
| 434610A | 2/1992 | (JP) . |
| WO94/00052 | 1/1994 | (WO) . |
| WO9502801 | 1/1995 | (WO) . |
| WO9520787 | 8/1995 | (WO) . |
| WO9520788 | 8/1995 | (WO) . |
| WO9616397 | 5/1996 | (WO) . |
| WO9622591 | 7/1996 | (WO) . |
| WO96/39944 | 12/1996 | (WO) . |

OTHER PUBLICATIONS

Millman, et al., "Design of a Four Degree–of–Freedom Force–Reflecting Manipulandum With a Specified Force/Torque Workspace," Proc. of the 1991 IEEE, CH2969–4/91/0000, pp. 1488–1493.

Brooks, Jr., et al., "Project GROPE—Haptic Displays for Scientific Visualization," Computer Graphics, vol. 24, No. 4, Aug. 1990, pp. 177–185.

Hannaford, B., et al., "Force–Feedback Cursor Control," NASA Tech Brief, vol. 13, No. 11, Item #21, Nov. 1989.

Hirota, et al., "Development of Surface Display," Dept. of Mechano–Informatics, Faculty of Engineering, University of Tokyo, 0–7803–1363–1/3, pp. 256–262.

(List continued on next page.)

Primary Examiner—Jeffery Brier
(74) Attorney, Agent, or Firm—James R. Riegel

(57) ABSTRACT

An apparatus for interfacing an elongated flexible object with an electrical system. The apparatus includes an object receiving portion and a rotation transducer coupled to the object receiving portion adapted to determine the rotational motion of the elongated flexible object when the object is engaged with the object receiving portion and to provide an electromechanical interface between the object and the electrical system. In a preferred embodiment, the rotation transducer includes an actuator and translational transducer to provide a translational electromechanical interface between the object and the electrical system.

23 Claims, 7 Drawing Sheets

U.S. PATENT DOCUMENTS

| | | | |
|---|---|---|---|
| 4,560,983 | 12/1985 | Williams | 340/825 |
| 4,571,834 | 2/1986 | Fraser et al. | 33/1 PT |
| 4,604,016 | 8/1986 | Joyce | 414/7 |
| 4,632,341 | 12/1986 | Repperger et al. | 244/230 |
| 4,638,798 | 1/1987 | Shelden et al. | 128/303 B |
| 4,654,648 | 3/1987 | Herrington et al. | 340/710 |
| 4,706,294 | 11/1987 | Ouchida | 381/109 |
| 4,712,101 | 12/1987 | Culver | 340/710 |
| 4,724,715 | 2/1988 | Culver | 74/471 R |
| 4,769,763 | 9/1988 | Trieb et al. | 364/559 |
| 4,787,051 | 11/1988 | Olson | 364/518 |
| 4,800,721 | 1/1989 | Cemenska et al. | 60/393 |
| 4,811,608 | 3/1989 | Hilton | 73/862.04 |
| 4,823,634 | 4/1989 | Culver | 74/471 XY |
| 4,868,549 | 9/1989 | Affinito et al. | 340/710 |
| 4,879,556 | 11/1989 | Duimel | 341/20 |
| 4,896,554 | 1/1990 | Culver | 74/471 XY |
| 4,907,970 | 3/1990 | Meenen, Jr. | 434/45 |
| 4,907,973 | 3/1990 | Hon | 434/262 |
| 4,949,119 | 8/1990 | Moncrief et al. | 364/578 |
| 4,961,138 | 10/1990 | Gorniak | 364/200 |
| 4,983,901 | 1/1991 | Lehmer | 318/685 |
| 5,007,085 | 4/1991 | Greanias et al. | 380/25 |
| 5,007,300 | 4/1991 | Siva | 74/471 XY |
| 5,044,956 | 9/1991 | Behensky et al. | 434/45 |
| 5,050,608 | 9/1991 | Watanabe et al. | 128/653 R |
| 5,072,361 | 12/1991 | Davis et al. | 364/167.01 |
| 5,076,517 | 12/1991 | Ferranti et al. | 244/228 |
| 5,095,303 | 3/1992 | Clark et al. | 340/710 |
| 5,103,404 | 4/1992 | McIntosh | 318/568.22 |
| 5,107,080 | 4/1992 | Rosen | 200/6 A |
| 5,116,051 | 5/1992 | Moncrief et al. | 273/448 B |
| 5,128,671 | 7/1992 | Thomas, Jr. | 341/20 |
| 5,132,672 | 7/1992 | Clark | 340/710 |
| 5,139,261 | 8/1992 | Openiano | 273/148 B |
| 5,142,931 | 9/1992 | Menahem | 74/471 XY |
| 5,143,505 | 9/1992 | Burdea et al. | 414/5 |
| 5,146,566 | 9/1992 | Hollis, Jr. et al. | 395/275 |
| 5,181,181 | 1/1993 | Glynn | 364/566 |
| 5,182,557 | 1/1993 | Lang | 341/20 |
| 5,184,319 | 2/1993 | Kramer | 364/806 |
| 5,185,561 | 2/1993 | Good et al. | 318/432 |
| 5,186,629 | 2/1993 | Rohen | 434/114 |
| 5,193,963 | 3/1993 | McAffee et al. | 414/5 |
| 5,197,003 | 3/1993 | Moncrief et al. | 364/410 |
| 5,203,563 | 4/1993 | Loper, III | 273/148 B |
| 5,220,260 | 6/1993 | Schuler | 318/561 |
| 5,223,776 | 6/1993 | Radke et al. | 318/568.1 |
| 5,228,356 | 7/1993 | Chuang | 74/471 XY |
| 5,230,623 | 7/1993 | Guthrie et al. | 433/72 |
| 5,235,868 | 8/1993 | Culver | 74/471 XY |
| 5,243,266 | 9/1993 | Kasagami | 318/568.1 |
| 5,251,127 | 10/1993 | Raab | 364/413.13 |
| 5,275,565 | 1/1994 | Moncrief | 434/29 |
| 5,286,203 | 2/1994 | Fuller et al. | 434/45 |
| 5,296,846 | 3/1994 | Ledley | 345/161 |
| 5,317,336 | 5/1994 | Hall | 345/164 |
| 5,351,692 | 10/1994 | Dow et al. | 128/662.06 |
| 5,354,162 | 10/1994 | Burdea et al. | 414/5 |
| 5,379,663 | 1/1995 | Hara | 74/471 XY |
| 5,381,080 | 1/1995 | Schnell et al. | 318/566 |
| 5,389,865 | 2/1995 | Jacobus et al. | 318/568.11 |
| 5,396,266 | 3/1995 | Brimhall | 345/161 |
| 5,402,582 | 4/1995 | Raab | 33/503 |
| 5,412,880 | 5/1995 | Raab | 33/503 |
| 5,414,337 | 5/1995 | Schuler | 318/561 |
| 5,429,140 | 7/1995 | Burdea et al. | 128/774 |
| 5,445,166 | 8/1995 | Taylor | 128/897 |
| 5,459,382 | 10/1995 | Jacobus et al. | 318/568.11 |
| 5,559,412 | 9/1996 | Schuler | 318/561 |
| 5,576,727 | 11/1996 | Rosenberg et al. | 345/179 |
| 5,587,937 | 12/1996 | Massie et al. | 364/578 |
| 5,589,828 | 12/1996 | Armstrong | 341/20 |
| 5,623,582 * | 4/1997 | Rosenberg . | |
| 5,629,594 | 5/1997 | Jacobus et al. | 318/568.11 |
| 5,634,794 | 6/1997 | Hildreth et al. | 34/37 |
| 5,642,469 | 6/1997 | Hannaford et al. | 395/99 |
| 5,643,087 | 7/1997 | Marcus et al. | 463/38 |
| 5,656,901 | 8/1997 | Kurita | 318/436 |
| 5,666,138 | 9/1997 | Culver | 345/161 |
| 5,696,537 | 12/1997 | Solhjell | 345/164 |
| 5,701,140 | 12/1997 | Rosenberg et al. | 345/156 |
| 5,709,219 | 1/1998 | Chen et al. | 128/782 |
| 5,739,811 | 4/1998 | Rosenberg et al. | 345/161 |
| 5,769,640 * | 6/1998 | Jacobus et al. . | |
| 5,790,108 | 8/1998 | Salcudean et al. | 345/184 |
| 5,821,920 * | 10/1998 | Rosenberg et al. . | |
| 5,880,714 | 3/1999 | Rosenberg et al. | 345/156 |
| 5,889,670 | 3/1999 | Schuler et al. | 364/186 |
| 5,889,672 | 3/1999 | Schuler et al. | 364/188 |
| 6,037,927 | 3/2000 | Rosenberg | 345/156 |
| 6,046,727 | 4/2000 | Rosenberg et al. | 345/156 |

OTHER PUBLICATIONS

Akamatsu, et al., "Multimodal Mouse: A Mouse–Type Device with Tactile and Force Display," Presence, vol. 3, No. 1, Winter 1994, pp. 73–80.

Kelley, et al., "MagicMouse: Tactile and Kinesthetic Feedback in the human–Computer Interface using an Electromagnetically Actuated Input/Output Device," Dept. of Electrical Engineering, University of British Columbia, Oct. 1993, pp. 1–27.

Iwata, Hiroo, "Artificial Reality with Force–feedback" Development of Desktop Virtual Space with Compact Master Manipulator, Inst. Of Engineering Mechanics, University of Tsukuba, Ibaraki, Computer Graphics, vol. 24, No. 4, Aug. 1990, pp. 165–170.

"3D Immersion Interface Tool," Immersion Probe™, 1993.

Wiker, Steven F. et al., "Development of Tactile Mice for Blind Access to Computers: Importance of Stimulation Locus, Object Size, and Vibrotactile Display Resolution," Proc. of the Human Factors Society 35th Annual Meeting, 1991, pp. 708–712.

Rosenberg, Louis B., "The Use of Virtual Fixtures to Enhance Operator Performance in Time Delayed Teleoperation", Crew Systems Directorate Biodynamics and Biocommunications Division Wright–Patterson, Air Force Material Command, Mar. 1993, pp. 1–45.

Jacobsen, S.C. et al., "High Performance, High Dexterity, Force Reflective Teleoperator II, ANS Topical Meeting on Robotics & Remote Systems," Albuquerque, New Mexico Feb. 24–27, 1991, pp. 1–10.

Kotoku, Tetsuo et al., "Environmental Modeling for the Interactive Display (EMID) Used in Telerobotic Systems," IEEE Nov. 3–5, 1991, pp. 99–1004.

Bejczy, Antal K., "The Phantom Robot: Predictive Displays for Teleoperation with Time Delay," IEEE 1990, pp. 546–550.

Buttolo, Pietro et al., "Pen–Based Force Display for Precision Manipulation in Virtual Environments," IEEE Mar. 1995, pp. 1–8.

Tan, Hong Z. et al., "Human Factors for the Design of Force–Reflecting Haptic Interfaces," Tan, Srinivasan, Eberman, & Chang, ASME WAM 1994, pp. 1–11.

Ellis, R.E. et al., "Design and Evaluation of a High–Performance Prototype Planar Haptic Interface," ASME Dec. 3, 1993, DSC—vol. 49, pp. 55–64.

Adelstein Bernard D. et al., "A High Performance Two Degree–of–Freedom Kinesthetic Interface," Massachusetts Institute of Technology 1992, pp. 108–112.

Colgate J. Edward et al., Implementation of Stiff Virtual Walls in Force–Reflecting Interfaces, Sep. 22, 1993.

Iwata, Hiroo et al, Volume Haptization, IEEE 1993, pp. 16–18.

Fischer, Patrick et al., "Specification and Design of Input Devices for Teleoperation," 1990.

Burdea, Grigore et al., "Distributed Virtual Force Feedback," IEEE, May 2, 1993, pp. 25–44.

Rosenberg, Louis B., "The Use of Virtual Fixtures as Perceptural Overlays to Enhance Operator Performance in Remote Environments," Air Force Material Command, Sep. 1992, pp. 1–42.

Rosenberg, Louis B., "Perceptual Design of a Virtual Rigid Surface Contact," Center for Design Reseach Stanford University, Air Force Material Command, Apr. 1993, pp. 1–41.

Rosenberg, Louis B. et al., "Perceptual Decomposition of Virtual Haptic Surfaces," IEEE, Oct. 1993.

Rosenberg, Louis B., "Virtual Haptic Overlays Enhance Performance in Telepresence Tasks," SPIE 1994.

Rosenberg, Louis B., "Virtual Fixtures as Tools to Enhance Operator Performance in Telepresence Environments," SPIE Telemanipulator Technology, 1993.

Colgate, J. Edward et al., "Implementation of Stiff Virtual Walls in Force–Reflecting Interfaces," 1993, pp. 1–9.

Yamakita, M. et al., Tele–Virtual Reality of Dynamic Mechanical Model, IEEE Jul. 7–10, 1992, pp. 1103–1110.

Adlestein, Bernard D. et al., "Design and Implementation of a Force Reflecting Manipulandum for Manual Control Research," 1992, pp. 1–24.

Ouh–young, Ming et al., "Force Display Performs Better than Visual Display in a Simple 6–D Docking Task," IEEE 1989, pp. 1462–1466.

Hannaford, Blake et al., "Performance Evaluation of a Six–Axis Generalized Force–Reflecting Teleoperator," IEEE May/Jun. 1991, vol. 21, No. 3, pp. 620–633.

Burdea, Grigore et al., "A Portable Dextrous Master with Force Feedback," Presence: Teleoperators and Virtual Environments, MIT Press, Jun. 1991.

Gotow, J.K., et al., "Perception of Mechanical Properties at the Man–Machine Interface," IEEE 1987, pp. 688–689.

Atkinston, William D. et al, "Computing with Feeling," Comput. & Graphics, vol. 2, No. 2–E, pp. 97–103.

Minsky, Margaret et al., "Feeling and Seeing: Issues in Force Display," ACM 1990, pp. 235–242.

Herndon, J.N. et al., "The State–of–the–Art Model M–2 Maintenance System," Proc. of the 1984 Nat'l Topical Meeting on Robotics and Remote Handling in Hostile Environments, American Nuclear Society, pp. 59–65.

Batter, James J. et al., "Grope–1: A Computer Display to the Sense of Feel," pp. TA–4–188–TA–4–192.

Noll, A. Michael, "Man–Machine Tactile Communication Dissertation," Polytechnic Institute of Brooklyn, Jun. 1971, pp. 1–88.

Ouh–Young, Ming, "Force Display in Molecular Docking," Chapel Hill 1990, pp. 1–85.

Ouh–young, Ming et al., "Using a Manipulator for Force Display in Molecular Docking," IEEE 1988, pp. 1824–1829.

* cited by examiner

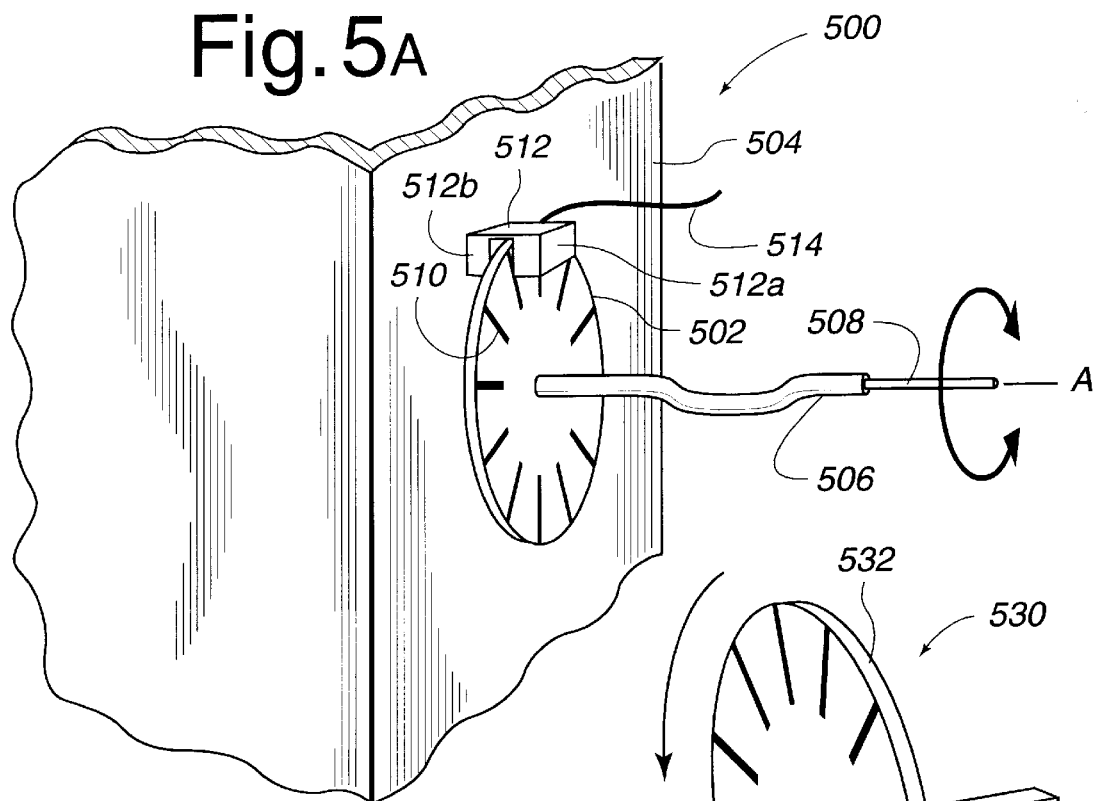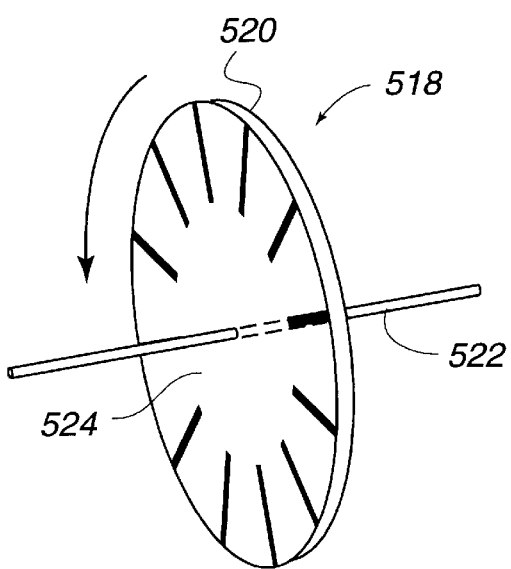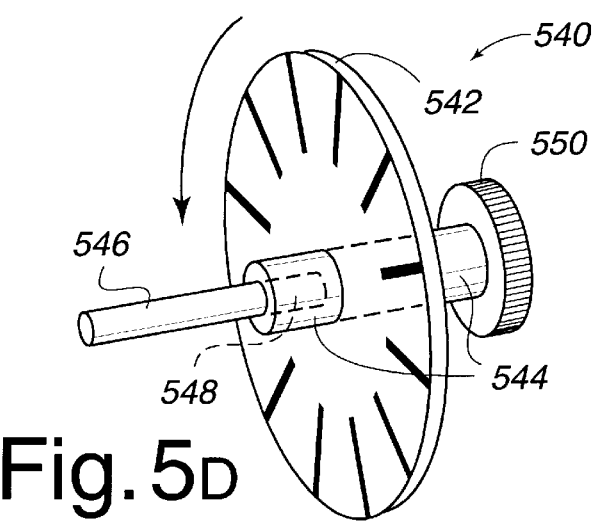

USER INTERFACE DEVICE INCLUDING BRAKING MECHANISM FOR INTERFACING WITH COMPUTER SIMULATIONS

CROSS REFERENCE TO RELATED APPLICATIONS

The present application is a continuation application of copending prior U.S. application Ser. No. 08/825,412, now U.S. Pat. No. 5,821,920, filed on Mar. 28, 1997, which is a continuation of U.S. application Ser. No. 08/344,148, filed on Nov. 23, 1994, abandoned, which is a continuation U.S. application Ser. No. 08/275,120, now U.S. Pat. No. 5,623,582, filed Jul. 14, 1994, the disclosures of which are incorporated herein by reference.

BACKGROUND OF THE INVENTION

1. The Field of the Invention

The present invention relates to human/computer interface input devices, and, more particularly, to computer input devices for simulating medical procedures.

2. The Relevant Art

Virtual reality computer systems provide users with the illusion that they are part of a "virtual" environment. A virtual reality system will typically include a computer processor, such as a personal computer or workstation, specialized virtual reality software, and virtual reality I/O devices such as head mounted displays, pointer gloves, three-dimensional ("3D") pointers and the like. Virtual reality computer systems have been used successfully for training in many fields, such as aviation and vehicle and systems operation. The appeal of using virtual reality computer systems for training relates in part to the ability of such systems to allow neophyte practitioners the luxury of operating in a highly realistic environment and making disastrous mistakes without consequence to the trainee, others or property. Thus, for example, a trainee pilot or automobile driver can learn to fly (or drive) using a virtual reality simulator without concern for accidents that would cause death and/or property damage in the real world. Similarly, operators of complex systems, e.g., nuclear power plants and weapons systems, can safely practice a wide variety of training scenarios that would risk life or property if performed in reality.

The advantages of simulation have not gone unnoticed in the medical field, which has become increasingly concerned with the costs of malpractice and inefficient care management. For example, a virtual reality computer system can allow a doctor-trainee or other human operator or user to "manipulate" a scalpel or probe within a computer-simulated "body", and thereby perform medical procedures on a virtual patient. In this instance, an I/O device as a scalpel or probe. As the "scalpel" or "probe" moves within the body, an image is displayed on the screen of the computer system, and the results of the pointer's movements are updated and displayed so that the operator can gain the experience of performing such a procedure without practicing on an actual human being or a cadaver.

For virtual reality systems to provide a realistic (and therefore effective) experience for the user, sensory feedback and manual interaction should be as natural as possible. As virtual reality systems become more powerful and as the number of potential applications increases, there is a growing need for specific human/computer interface devices which allow users to interface with computer simulations with tools that realistically emulate the activities being represented within the virtual simulation. Such procedures as laparoscopic surgery, catheter insertion, and epidural analgesia should be realistically simulated with suitable human/computer interface devices if the doctor is to be properly trained.

While the state of the art in virtual simulation and medical imaging provides a rich and realistic visual feedback, there is a great need for new human/computer interface tools which allow users to perform natural manual interactions with the computer simulation. For medical simulation, there is a strong need to provide doctors with a realistic mechanism for performing the manual activities associated with medical procedures while allowing a computer to accurately keep track of their actions. In addition to tracking a user's manual acivity and feeding such information to the controlling computer to provide a 3D visual represtation to the user, a human interface mechanism should also provide force feedback to the user, so the user can obtain realistic tactile information as well. Thus an effective human interface not only acts as an input device for tracking motion, but also as an output device for producing realistic tactile (haptic) sensations.

There are number of devices that are commercially available for interfacing a human with a computer for virtual reality simulations. There are, for example, such 2-dimensional input devices such as mice, trackballs, and digitizing tablets. However, 2-dimensional input devices tend to be awkward and inadequate to the task of interfacing with 3-dimensional virtual reality simulations. In contrast, a 3-dimensional human/computer interface tool, sold under the trademark Immersion PROBE™ is marketed by Immersion Human Interface Corporation of Palo Alto, Calif., allows manual control in 3-dimensional virtual reality computer environments. A pen-like stylus allows for dexterous 3-dimensional manipulation, and the position and orientation of the stylus is communicated to a host computer. The Immersion PROBE has six degrees of freedom which convey spatial coordinates (x, y, z) and orientation (role, pitch, yaw) of the stylus to the host computer.

While the Immersion PROBE is an excellent 3-dimensional interface tool, it may be inappropriate for certain virtual reality simulation applications. For example, in some of the aforementioned medical simulations three or four degrees of freedom for a 3-dimensional human/computer interface tool is sufficient and, often, more desirable than five or six degrees of freedom because it more accurately mimics the real-life constraints of the actual medical procedure.

The application of virtual reality simulation to the operation of catheters, and other elongated flexible objects, often require only two, three or four degrees of freedom. In particular, catheters work in a largely two dimensional environment created by the channel into which the catheter is inserted, e.g., a vein or artery. The forces to which a catheter is subjected often are simplified compared to other medical implements, consisting mainly of drag forces. Therefore, a less complex virtual reality device is desirable for certain applications.

SUMMARY OF THE INVENTION

The present invention provides a human/computer interface tool which is particularly well adapted to simulations requiring between two and four degrees of freedom, and especially two degrees of freedom, such as for simulations of catheter procedures. Thus, it will be appreciated that the present invention provides a less complex, more compact, lighter weight, lower inertia and less expensive alternative to a six degree of freedom human/computer interface tool than heretofore available. In particular, the present invention includes a means for providing to a user a highly realistic force feedback to produce the sorts of tactile sensations assoicated with catheter procedures.

In one embodiment, the present invention includes an apparatus for interfacing the motion of an elongated flexible object capable of translation and rotation with an electrical system, which apparatus includes (a) an object receiving portion and (b) a rotation transducer coupled to the object receiving portion, which rotation transducer is adapted to determine rotational motion of the elongated flexible object; thereby providing an electromechanical interface between the elongated flexible object and the electrical system. An especially preferred embodiment is one wherein the electrical system is a digital electrical system.

In a preferred embodiment, the rotation transducer comprises a disk including an aperture dimensioned to receive the elongated flexible object. The disk is coupled with a hollow shaft that is dimensioned to engagedly receive the object. The hollow shaft includes at least one bend. The shaft may further include at least two substantially parallel sections. In one especially preferred embodiment, the hollow shaft includes two bends in substantially opposing directions and three substantially parallel sections. In still another preferred embodiment, the apparatus of the invention includes an actuator to engage the elongated flexible object and a translation transducer coupled to the object receiving portion which is adapted to determine translational motion of the elongated flexible object.

In a preferred alternative embodiment, a second actuator and a second transducer are coupled to the object receiving portion and are disposed between the actuator and the translation transducer and the rotation transducer. In still another alternative embodiment, the apparatus of the invention is mounted on a gimbal apparatus including a support and a gimbal mechanism having a base, a first portion of which base is rotatably mounted to the support and a second portion of which base is rotatably mounted to the object receiving portion. An actuator and translation and rotation transducers are further coupled with the object receiving portion. The rotation transducer includes a disk including an aperture dimensioned to receive the elongated flexible object. The disk is coupled with a hollow shaft that is dimensioned to engagedly receive the object. The hollow shaft includes at least one bend.

In yet another aspect, the present invention includes a human/computer interface including a shaft receiving portion; an elongated flexible shaft engaged with the shaft receiving portion having a grip area to be grasped by the operator, a first sensor to detect translational motion of the shaft; and a second sensor to detect rotational motion of the shaft, wherein the second sensor includes a disk including an aperture dimensioned to receive the elongated flexible object The disk is coupled with a hollow shaft that is dimensioned to engagedly receive the object. The hollow shaft includes at least one bend.

These and other advantages of the present invention will become apparent to those skilled in the art upon a reading of the following descriptions of the invention and a study of the several figures of the drawings.

BRIEF DESCRIPTION OF THE DRAWINGS

FIG. 2 illustrates an apparatus for interfacing the motion of an elongated flexible object, including rotation and translation transducers. FIG. 2A is an illustration of an actuator for engaging an elongated flexible object FIG. 2B is an illustration of a device for determining the translation of an elongated flexible object.

FIG. 3A illustrates a side view of the shaft, including a depression of depth "D". FIG. 3B is a cross section of FIG. 3A, taken along the line 3B—3B.

FIG. 4A illustrates a side view of the shaft, having a bend of depth "D". FIG. 4B is an illustration of a cross section taken along line 4B—4B as the shaft is rotated through 360°.

FIGS. 5A, 5B, 5C, 5D, 5E, 5F and 5G illustrate rotation sensors in accordance with the present invention. FIG. 5A illustrates one embodiment of a rotational sensor of the invention including a shaft coupled to a disk. FIG. 5B illustrates a second rotational sensor including a disk having an aperture dimensioned to engagedly receive a shaft. FIG. 5C illustrates another rotational sensor embodiment wherein a disk includes a key dimensioned to receive a shaft having a flat. FIG. 5D illustrates a rotational sensor fixedly coupled to a shaft. FIGS. 5E, 5F and 5G each illustrate an embodiment of the invention wherein the rotation of a shaft is determined using an optical encoder.

DESCRIPTION OF SPECIFIC EMBODIMENTS

Figure 1:
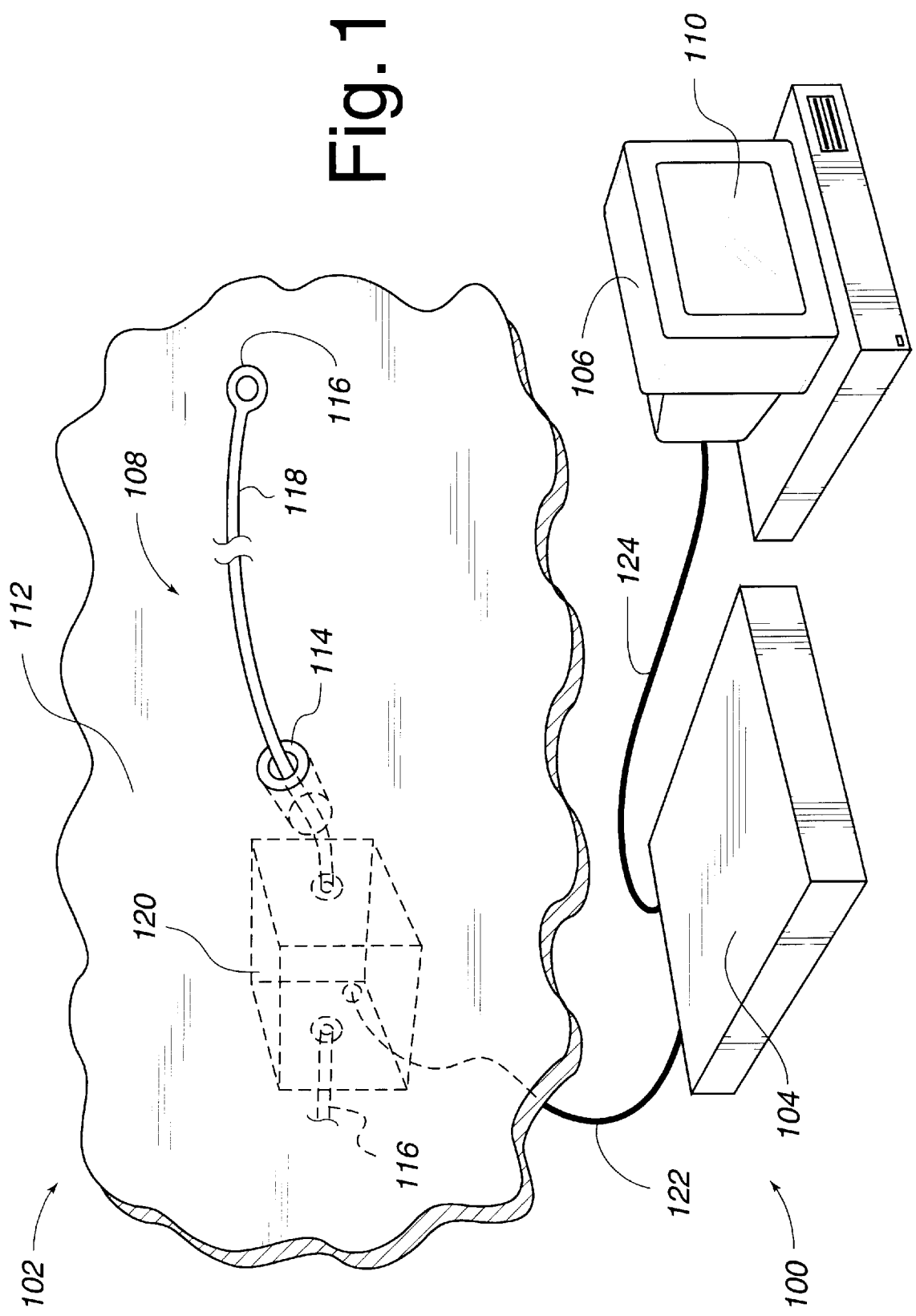
FIG. 1 is an illustration of a computer/human interface system in accordance with the present invention.

In FIG. 1, a virtual reality system 100 used to simulate a medical procedure including a human/computer interface apparatus 102, a electronic interface 104 and a computer 106 is shown. The illustrated virtual reality system 100 is directed to a virtual reality simulation of a catheter procedure. The software of the simulation is not a part of this invention and thus will not be discussed in any detail. However, such software is commercially available. Suitable software drivers which interface such simulation software with computer input/output (I/O) devices are also available commercially, e.g., from Immersion Human Interface Corporation of Palo Alto, Calif., USA.

A catheter 108 used in conjunction with the present invention is manipulated by an operator and virtual reality images are displayed on a screen 110 of the digital processing system in response to such manipulations. Preferably, the digital processing system is a personal computer or workstation, such as an IBM-PC AT or Macintosh personal computer, or a SUN or Silicon Graphics workstation. Most commonly, the digital processing system is a personal computer which operates under the MS-DOS operating system in conformance with an IBM PC AT standard.

In addition to a standard catheter 108, the human/interface apparatus 102 includes a barrier 112 and a "central line" 114 through which the catheter is inserted into the body. The barrier 112 is used to represent portion of the skin covering the body of a patient. Preferably barrier 112 is formed from a mannequin or other life-like representation of a body or body portion, e.g., the torso, arm or leg. Central line 114 is inserted into the body of the patient to provide an entry and removal point from the body of the patient for the catheter 108, and to allow the manipulation of the distal portion of the catheter 108 within the body of the patient while minimizing tissue damage. Catheter 108 and central line 114 are commercially available from sources such as Target Therapeutics of Fremont, Calif., USA and U.S. Surgical of Connecticut, USA. Preferably, the catheter 108 is modified such that the end of the tool (such as any cutting edges) are removed, leaving only the handle and the shaft. The end of the catheter tool 108 is not required for the virtual reality simulation, and is removed to prevent any potential damage to persons or property.

The catheter 108 includes a handle or "grip" portion 116 and a shaft portion 118. The grip portion can be any conventional device used to manipulate the catheter, or the grip may comprise the shaft portion itself. The shaft portion is an elongated flexible object and, in particular, is an elongated cylindrical object. The present invention is concerned with tracking the movement of the shaft portion 118 in three-dimensional space, where the movement has been constrained such that the shaft portion 118 has only two, three or four degrees of motion. This is a good simulation of the typical use of a catheter 108 in that once the catheter is inserted into a patient, it is limited to about two degrees of freedom. More particularly, the shaft 118 is constrained at some point of along its length such that it can move with two degrees of freedom within the patient's body.

While the present invention will be discussed with reference to the shaft portion 118 of catheter tool 108, it will be appreciated that a great number of other types of objects can be used with the method and apparatus of the present invention. In fact, the present invention can be used with any elongated mechanical object where it is desirable to provide a human/computer interface with three or four degrees of freedom. Such objects may include catheters, hypodermic needles, wires, fiber optic bundles, screw drivers, pool cues, etc. Furthermore, although the described preferred embodiment of the present invention contemplates the use of a elongated cylindrical mechanical object, other embodiments of the present invention provide a similar human/computer interface for an elongated mechanical objects which are not cylindrical in shape.

The electronic interface 104 is a part of the human/computer interface apparatus 102 and couples the apparatus 102 to the computer 106. More particularly, interface 104 is used in preferred embodiments to couple the various actuators and sensors contained in apparatus 102 (which actuators and sensors are described in detail below) to computer 106. An electronic interface 104 that is particularly well adapted for the present is described in U.S. patent application Ser. No. 08/092,974, now issued as U.S. Pat. No. 5,576,727 filed Jul. 16, 1993 and entitled "3-D Mechanical Mouse" which application is assigned to the assignee of the present invention and incorporated herein by reference in its entirety. The electronic interface described therein was designed for the Immersion PROBE™ 3-D mechanical mouse and has six channels corresponding to the six degrees of freedom of the Immersion PROBE. However, in the context of the present invention, the electronic interface 104 requires the use of only two, three or four of the six channels, since the present invention is preferably constrained to no more than two, three or four degrees of freedom.

The electronic interface 104 is coupled to a human/computer interface apparatus 120 of the apparatus 102 by a cable 122 and is coupled to the computer 106 by a cable 124.

In some embodiments of the present invention, interface 104 serves solely as an input device for the computer 106. In other embodiments of the present invention, interface 104 serves solely as an output device for the computer 106. In yet other embodiments of the present invention, the interface 104 serves as an input/output (I/O) device for the computer 106.

Figure 2:
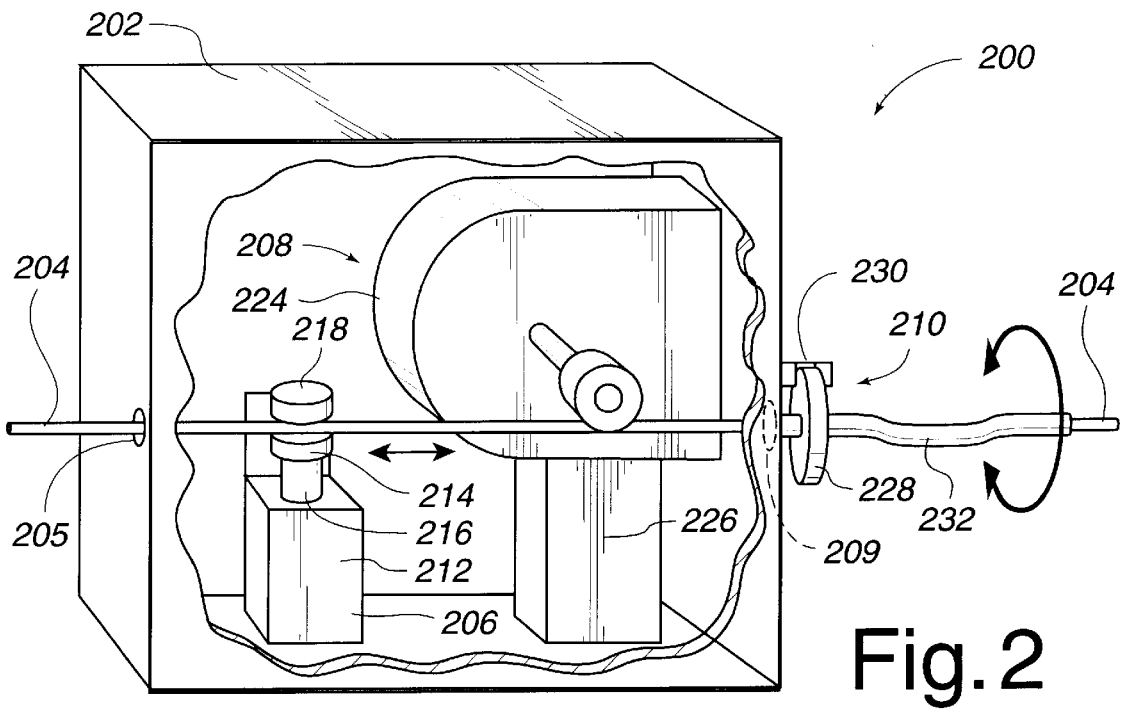
FIGS. 2, 2A and 2B are illustrations of an apparatus for interfacing the motion of an elongated flexible object capable of translation and rotation with a computer system.

Apparatus 120 is shown in greater detail at 200 in FIG. 2. Apparatus 200 includes an object receiving portion 202 into which an elongated flexible object 204, such as a catheter, is introduced through aperture 205. Elongated flexible object 204 passes through the interior of object receiving portion 202, the interior of which receiving portion includes one or more electromechanical transducers coupled with the object receiving portion and associated with the elongated flexible object, such as actuator 206 and translation transducer 208. The elongated flexible object 204 exits the object receiving portion 202 through a second aperture 209 whereupon the elongated flexible object passes through rotational transducer 210 which rotational transducer is rotatably coupled to the object receiving portion.

The object receiving portion 202 is preferably fashioned from a unitary mass of material made from aluminum or some other lightweight material, such as a plastic, that preferably is cast, molded, and/or machined as a monoblock member having the aforementioned actuator, translation transducer and rotation transducer. The object receiving portion can also be a housing to which various acutators, transducers and sensors are coupled.

The terms "associated with", "related to", or the like are meant to indicate that the electromechanical transducer is influenced by or influences one of the degrees of freedom of the elongated flexible object 204. The electromechanical transducers can be input transducers, in which case they sense motion along a respective degree of freedom and produce an electrical signal corresponding thereto for input into computer 106. Alternatively, the electromechanical transducers can be output transducers which receive electrical signals from computer 106 that cause the transducers to impart a force on the object in accordance with their respective degrees of freedom. The electromechanical transducers can also be hybrid or bi-directional transducers which operate both as sensors and as actuator devices.

A variety of transducers, readily available in the commercial market, are suitable for use in the present invention. For example, if the transducers are input transducers ("sensors"), such sensors can include encoded wheel transducers, potentiometers, optical encoders, etc. Output transducers ("actuators") include stepper motors, servo motors, magnetic particle brakes, friction brakes, pneumatic actuators, etc. Hybrid or bi-directional transducers often pair input and output transducers together, but may also include a purely bi-directional transducer such as a permanent magnet electric motor/generator.

It should be noted that the present invention can utilize both absolute and relative sensors. An absolute sensor is one which the angle of the sensor is known in absolute terms, such as with an analog potentiometer. Relative sensors only provide relative angle information, and thus require some form of calibration step which provides a reference position for the relative angle information. The sensors described herein are primarily relative sensors. In consequence, there is an implied calibration step after system power-up wherein the shaft is placed in a known position within the gimbal mechanism and a calibration signal is provided to the system to provide the reference position mentioned above. All angles provided by the sensors are thereafter relative to that reference position. Such calibration methods are well known to those skilled in the art and, therefore, will not be discussed in any great detail herein.

In a preferred embodiment, actuator 206 is a solenoid comprising a base/sensor portion 212 to which is coupled a lower interface 214 by a shaft 216. The lower interface portion 214 engages elongated flexible object 204 against upper interface portion 218 by applying a force in a direction substantially perpendicular to the direction of translation of the elongated flexible object 204, which direction is indicated by the linear bi-directional arrow, to produce thereby a frictional force along the direction of translation of the object 204. Such solenoids are available commercially from, e.g., Guardian Electric (Woodstock, Ill., USA). It will be appreciated that other actuator devices may be employed in the invention, e.g., magnetic particle brakes, such as those available commercially from, e.g., Force Limited (Santa Monica, Calif., USA). In addition actuator 206 can also be a pneumatic or hydraulic device which applies a force to elongated flexible object 204. It will be appreciated by those of skill in the art that the choice of a electromechanical, electromagnetic, pneumatic or hydraulic actuator will depend in part on the response time, cost and complexity of the device. Preferably, the actuator has a response time suitable for realistic simulations (i.e., a fast response time), a low cost and low complexity. Electromechanical/electromagnetic transducers are preferred as they typically have a fast response time, low cost are smaller and simpler than hydraulic and pneumatic devices performing the same or similar function.

Figure 2A:
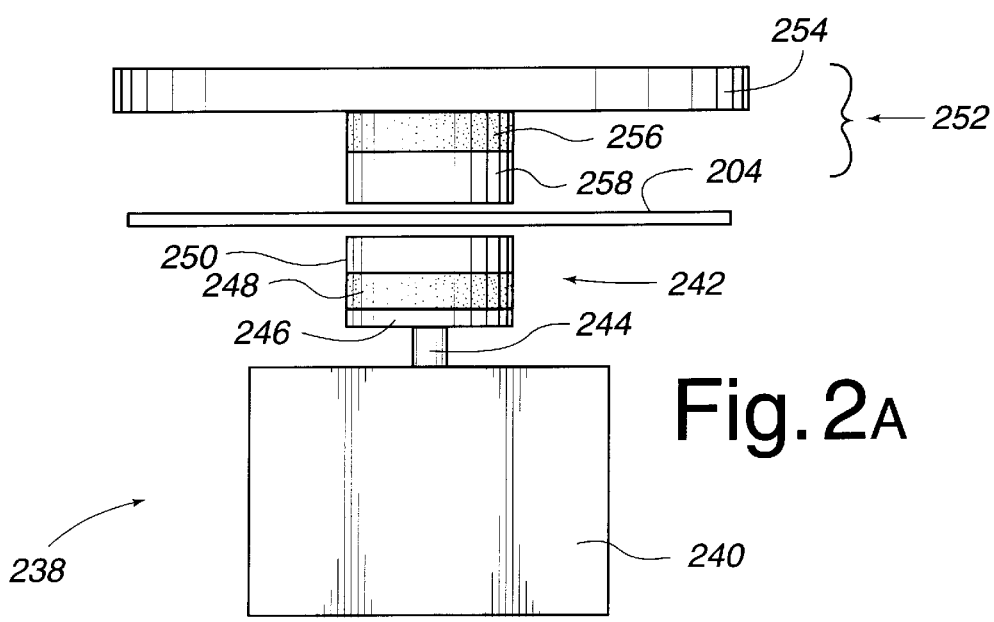

FIG. 2A illustrates a preferred solenoid embodiment at 238. Solenoid 238 includes a base/sensor portion 240 which is coupled with a lower interface 242 through a reciprocating shaft 244. Lower interface 242 comprises a platform 246 which is coupled with shaft 244 and upon which platform is coupled an optional resilient pad 248 and a brake pad 250. Resilient pad 248 comprises a substance which effective to act as a shock absorber, such as rubber, and is optional. Brake pad 250 comprises a substance which is effective to stop or slow the translational motion of elongated flexible object 204 when the lower interface 242 engages the elongated flexible object 204 against upper interface 252. The materials appropriate for the optional shock absorber and brake pad will be apparent to those of skill in the art. Upper interface 252 includes a fixed support 254 which may be coupled to the object receiving portion or to the base/sensor 240. To the fixed support 254 is coupled a second resilient pad 256 and a second brake pad 258, both of which are comprised of the same materials as resilient pad 246 and brake pad 250.

Figure 2B:
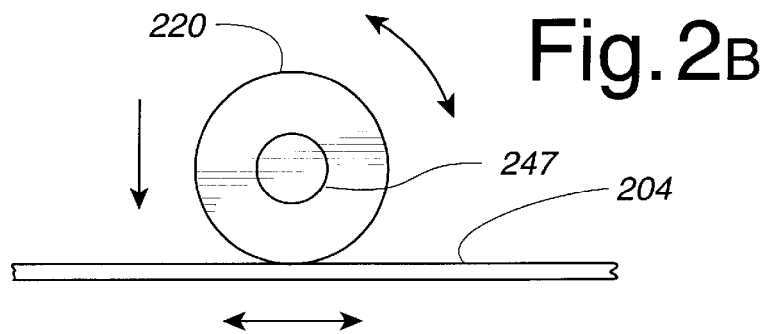

Referring back to FIG. 2, in a preferred embodiment, translation transducer 208 includes a wheel 200 which wheel is mounted on a shaft 222 coupled to a sensor 224 which sensor is coupled to object receiving portion 202 by a base 226. Translation transducer 208 is adapted to determine translational motion of elongated flexible object 204 by sensing positions of the elongated flexible object along the direction of translation thereof and producing electrical signals corresponding to the positions, as illustrated in FIG. 2B. Wheel 220 engages elongated flexible object 204 with a normal force (downward arrow) such that translation of elongated flexible object 204 (indicated by the bi-directional linear arrow) causes rotation of shaft end 247 (indicated by the bi-directional curved arrow) creating an electrical signal from sensor 224 (not shown) which is recorded by interface 104 (also not shown). It will be appreciated that translation transducer 208 could also be an output transducer (actuator) and apply a frictional braking force to elongated object 204 to simulate such effects as drag experienced by the catheter as the catheter traverses various vessels in the body. Such transducers are well known in the art and available commercially. One preferred transducer is an optical encoder model SI marketed by U.S. Digital of Vancouver, Wash. USA. This transducer is an encoded wheel type input transducer. A preferred output transducer for use of the present invention is a d.c. motor model 2434.970-50 produced by Maxon of Fall River, Mass. USA. This type of transducer is a servo motor type output transducer.

Referring back to FIG. 2, rotation transducer 210 is rotatably coupled to object receiving portion 202 to determine the rotational motion of elongated flexible object 204. Rotational transducer 210 includes a disk 228 coupled with a hollow shaft 232. Preferably, the disk and hollow shaft are attached, e.g., by gluing or press fitting, to provide a substantially unitary device. The disk 228 includes an aperture (not shown) dimensioned to receive the elongated flexible object and the hollow shaft is dimensioned to receivably engage the elongated flexible object such that disk 228 substantially tracks the rotational motion of the elongated flexible object 204; yet provides minimal translational friction. As the disk rotates in response to the rotational motion of the elongated flexible object, the rotation of the disk is detected by sensor 230, as will be described in greater detail below.

Figure 3A:
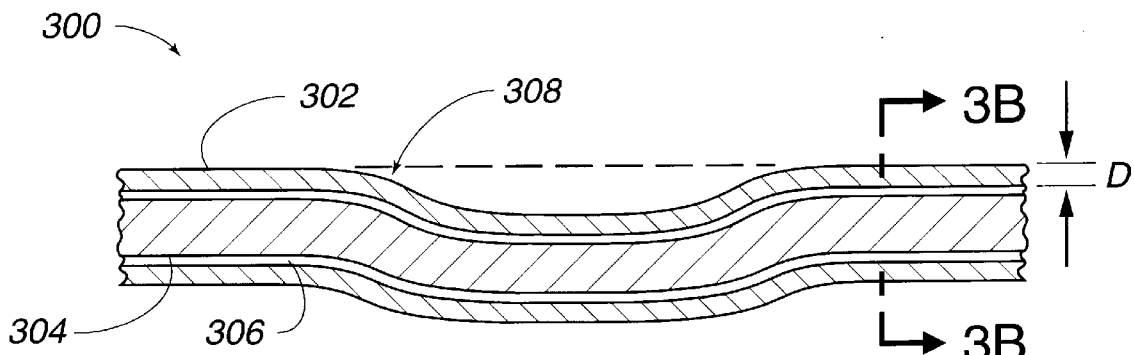
FIGS. 3A and 3B illustrate a hollow shaft used for determining the rotation of an elongated flexible object.

Hollow shaft 232 is illustrated in greater detail in FIG. 3A which provides a cut-away view of the elongated object and the hollow shaft at 300. Hollow shaft 302 is preferably made from stainless steel. The hollow shaft is dimensioned to engagably receive elongated object 304 with a gap 306 between hollow shaft 302 and elongated flexible object 304 sufficient to allow translation of the elongated flexible object without substantial interference from the interior surface of the hollow shaft; yet small enough that the hollow shaft rotates substantially continuously with the elongated flexible object.

Figure 3B:
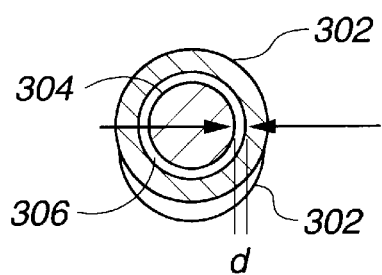

Gap 306 is further illustrated in FIG. 3B, a cut-away view taken along the line 3B—3B of FIG. 3A, where the size of the gap is denoted "d". Generally d is chosen such that the hollow and shaft and the elongated flexible object have a tight engaging fit. Preferably the diameter of the hollow shaft is between about 120% and about 150% of the diameter of the elongated flexible object, i.e., the size of the gap is between about 20% and about 50% of the diameter of the elongated flexible object. For example, where the elongated flexible object has a diameter of about 0.02 inches, preferred values for d are between about 0.001 inches and about 0.010 inches and, more preferably, between about 0.003 inches and about 0.006 inches. The hollow shaft can further include substances to increase or decrease the friction between the interior wall of the hollow shaft and the surface of the elongated flexible object. Such substances are known to persons of skill in the art.

Referring back to FIG. 3A, hollow shaft 302 further includes at least one bend, such as that shown generally at 308, where two bends in substantially opposite directions are illustrated. In preferred embodiments one or two bends included in the hollow shaft. Preferably the sections of the hollow shaft on each side of the bend(s) are substantially parallel. The bend(s) function to allow the hollow shaft and disk 228 to track the rotational motion of the elongated flexible object while offering little impedance to the translational movement of the elongated flexible object.

The depth of the bend is denoted by "D". Generally D is chosen such that the hollow shaft and elongated flexible object have the desired rotation tracking and translation characteristics. It has been found that preferred values for D depend on several factors, including the stiffness of the elongated object and the tightness of fit between the hollow shaft and the elongated flexible object. Stiffer elongated objects typically require a smaller value of D to achieve desirable rotation and translation properties for a given gap d than more flexible objects having the same value of d. For example, for values of d between about 0.002 and 0.010 inches, D is preferably between about 0.05 and about 0.20 inches, respectively.

Figure 4A:
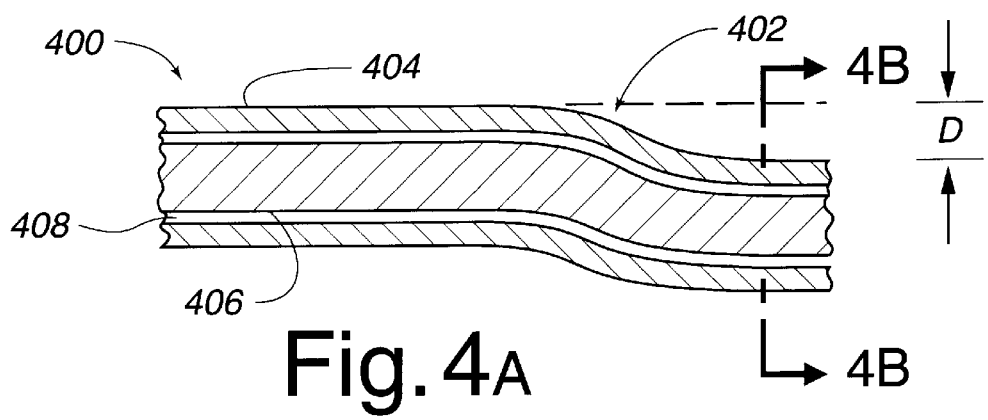
FIGS. 4A and 4B illustrate a second configuration of a shaft used to determine the rotation of an elongated flexible object.
Figure 4B:
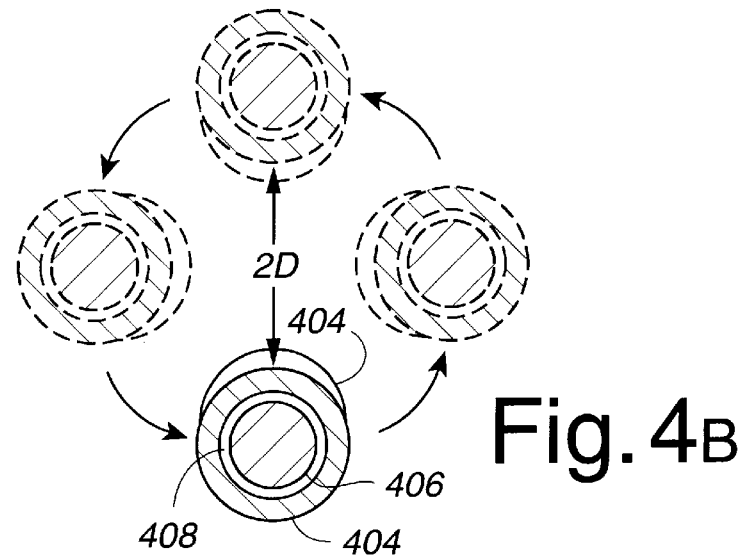

FIG. 4A illustrates a second preferred embodiment of the hollow shaft at 400, wherein a single bend 402 is placed in hollow shaft 404, which hollow shaft includes elongated flexible object 406 and gap 408, to divide the hollow shaft into two substantially parallel sections. FIG. 4B illustrates a cut-away view taken along line 4B—4B of FIG. 4A as the hollow shaft and elongated flexible object are rotated through 360°.

FIG. 5A at 500 illustrates a preferred embodiment of rotation transducer 210 of FIG. 2. In a preferred embodiment, rotation transducer 500 includes a disk 502 rotatably coupled with object receiving portion 504 for rotation by hollow shaft 506 and elongated flexible object 508. The disk is preferably made from a clear, plastic material and is provided with a number of dark radial bands 510 near its circumference, such as by printing or silk screening. A photodetector pair 512 including a light source 512a and a detector 512b are positioned on opposing sides of disk 502 in alignment with the bands 510. As disk 502 rotates around an axis A, the bands 510 alternatively allow light emanating from light source 512a to impinge or not impinge upon the detector 512b. The electronic interface 104, coupled to the photodetector 512 by cable 514, counts the bands 510 as they pass the photodetector 512b to provide a signal on cable 122 to the computer 106 indicating the rotational position of the hollow shaft 506 and elongated flexible object 508 around axis A. The photodetector may also be provided as two pairs of photodetectors to determine the direction of rotation, as is well known to those skilled in the art of sensor design and described in co-pending U.S. patent application Ser. No. 08/275,120.

FIG. 5B illustrates an alternate embodiment of the rotation transducer at 518, wherein disk 520 tracks the rotation of shaft 522 extending engagably through an aperture 524 in disk 520. The engagement between shaft 522 and disk aperture 524 preferably is accomplished by the formation of a frictional seal between the disk aperture and shaft, as described in greater detail in co-pending U.S. patent application Ser. No. 08/275,120 now U.S. Pat. No. 5,623,582. FIG. 5C illustrates a second alternate embodiment at 530, wherein disk 532 is engaged with shaft 534 including a flat 535, which shaft extends through a key way 536 dimensioned to receivably engage shaft 534 and flat 535. This embodiment is also discussed in U.S. patent application Ser. No. 08/275,120. Both disks 520 and 532 include dark radial bands near their circumferences to be used in conjunction with a photodetector as described above.

In yet another alternate preferred embodiment, shown in FIG. 5D at 540, the rotation transducer comprises a disk 542 including a sleeve 544 dimensioned to receive and fixedly hold an end portion 548 of shaft 546. The sleeve is rotatably coupled to a bearing 550 which bearing is coupled to a wall of the object receiving portion. Disk 542 is preferably provided with a number of dark radial bands near its circumference, such as by printing or silk screening, for use with an optical rotation detector as just described. It will be appreciated, however, that this embodiment does not allow translation of shaft 546 through disk 542.

Figure 5E:
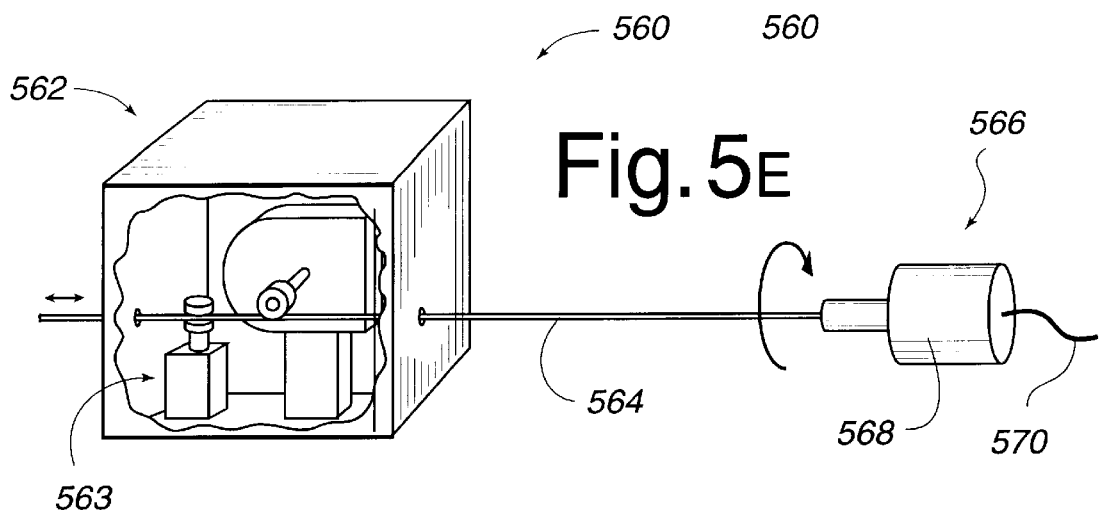
Figure 5F:
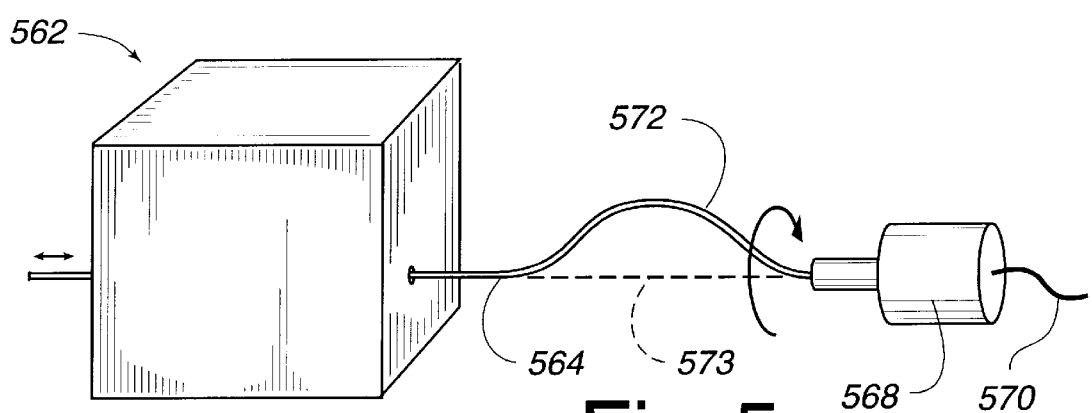
Figure 5G:
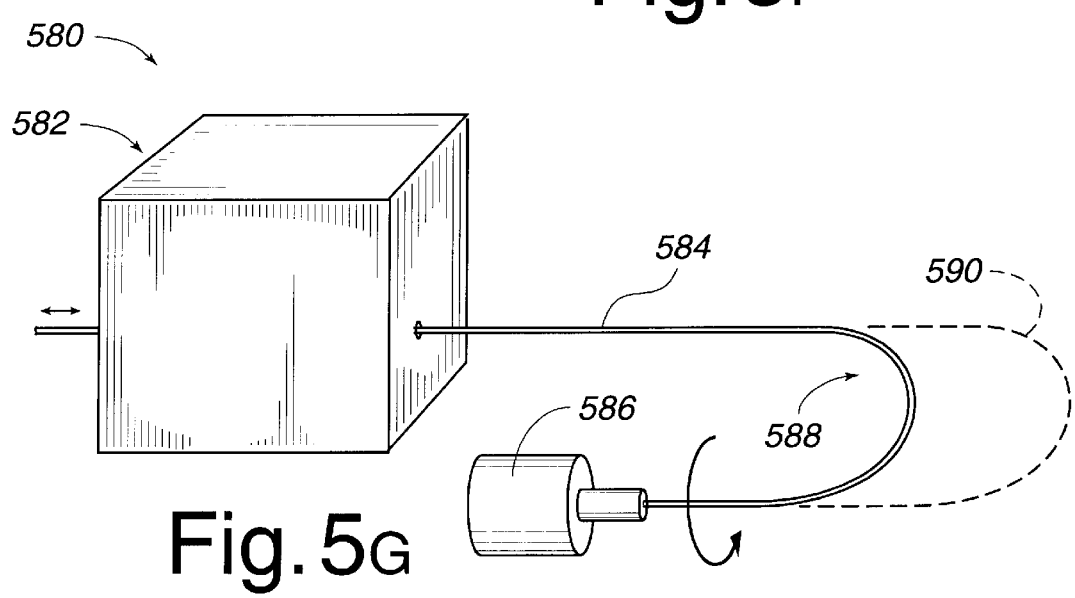

Two additional alternative embodiments are described with respect to FIGS. 5E, 5F and 5G. FIG. 5E at 560 illustrates an embodiment wherein object receiving portion 562, including an actuator and translation transducer shown generally at 563 and as described above with respect to FIG. 2, contact shaft 564 which shaft is fixedly engaged with a fixed rotary sensor 566, the sensor comprising an optical encoder 568 which is coupled by a connection 570 to interface 104. Rotational motion at the end of the shaft 564 (see arrow) is sensed by the optical encoder which transmits signals to the interface for analysis by computer 106. Translational motion is also accommodated as illustrated in FIG. 5F. There, translation of the wire in the direction of the optical encoder causes buckling of the wire as illustrated by the raised portion of the curve 572. Translation away form the encoder returns the wire to a substantially taught, substantially straight, condition as illustrated by the dashed line. Translational motion in either direction is detected as described above. Optical encoders and their interfacing with computer devices are known to those of skill in the art.

FIG. 5G illustrates an alternate embodiment at 580 wherein the object receiving portion 582 which fixedly receives shaft 564 is positioned laterally from optical encoder 586 to threby create a bend in shaft 584 as indicated at 588. Rotational motion at the distal end of the shaft is sensed at the optical encoder while translational motion is sensed as described above. The translational motion of the shaft in the direction of the optical encoder is accommodated by the extension of the bend of the shaft from the position shown at 588 (solid line) to 590 (dashed line). Again, the use of optical encoders is known to those of skill in the art.

In some applications, it will be preferable to link two apparatuses of the invention in tandem. For example, in an "epidural" procedure, the physician or practitioner first inserts a large bore needle into the patient through which needle a catheter is inserted. Thus, simulation of an epidural procedure requires simulating independently the responses associated with the insertion of the needle and the responses associated with the insertion of the catheter.

Figure 6:
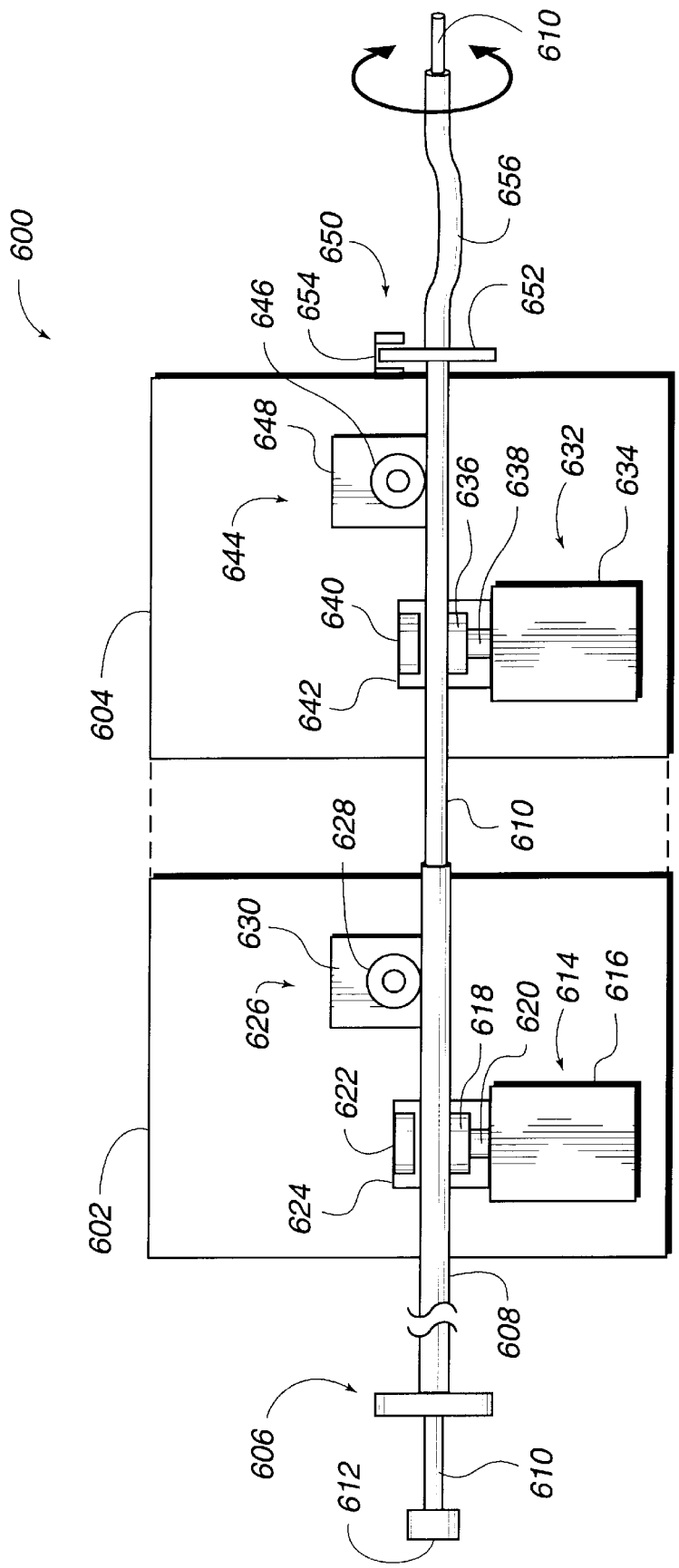
FIG. 6 is an illustration of two apparatuses of the invention arranged in a tandem configuration.

A preferred tandem configuration for simulating a procedure such as an epidural procedure is shown in FIG. 6 at 600. First and second object receiving portions 602 and 604 respectively are placed in an adjoining configuration, indicated by the dashed lines, and are substantially identical to object receiving portion 202 described above with respect to FIG. 2. Both object receiving portions 602 and 604 are adapted to receive "epidural" device 606, which device includes external shaft 608 and elongated flexible object 610 which object can be coupled to an external control such as handle 612. Within object receiving portion 602 is preferably included actuator 614, which actuator includes a base/sensor 616, a lower interface portion 618 and a shaft 620, in addition to upper interface portion 622 which is coupled to support 624. Object receiving portion 602 also preferably includes translation transducer 626, which transducer includes wheel 628 and sensor 630. Similarly, object receiving portion 604 includes preferably actuator 632, which actuator includes a base/sensor 634, a lower interface portion 636 and a shaft 638, in addition to upper interface portion 640 which is coupled to support 642. Object receiving portion 604 also preferably includes translation transducer 644, which transducer includes wheel 646 and sensor 648. The actuators and transducers, and their respective components, are all substantially identical to those described above with respect to FIG. 2.

Object receiving portion 604 is further rotatably coupled to rotation transducer 650, which transducer includes disk 652 and sensor 654. Disk 652 is coupled to hollow shaft 656 which is dimensioned to engagably receive elongated flexible object 610. Rotation transducer 650, including disk 652, sensor 654 and hollow shaft 656 are of substantially identical to those analogous components discussed above with respect to FIG. 5A. It will be appreciated that the alternative rotation sensor embodiments discussed above with resepct to FIGS. 5B–5G can be used as well.

In addition to the configuration shown in FIG. 6, a second preferred configuration, not shown, is one wherein either actuator 614 or transducer 626 is omitted. It will also be appreciated that the actuators and transducers may be combined in a single object receiving portion.

Figure 7:
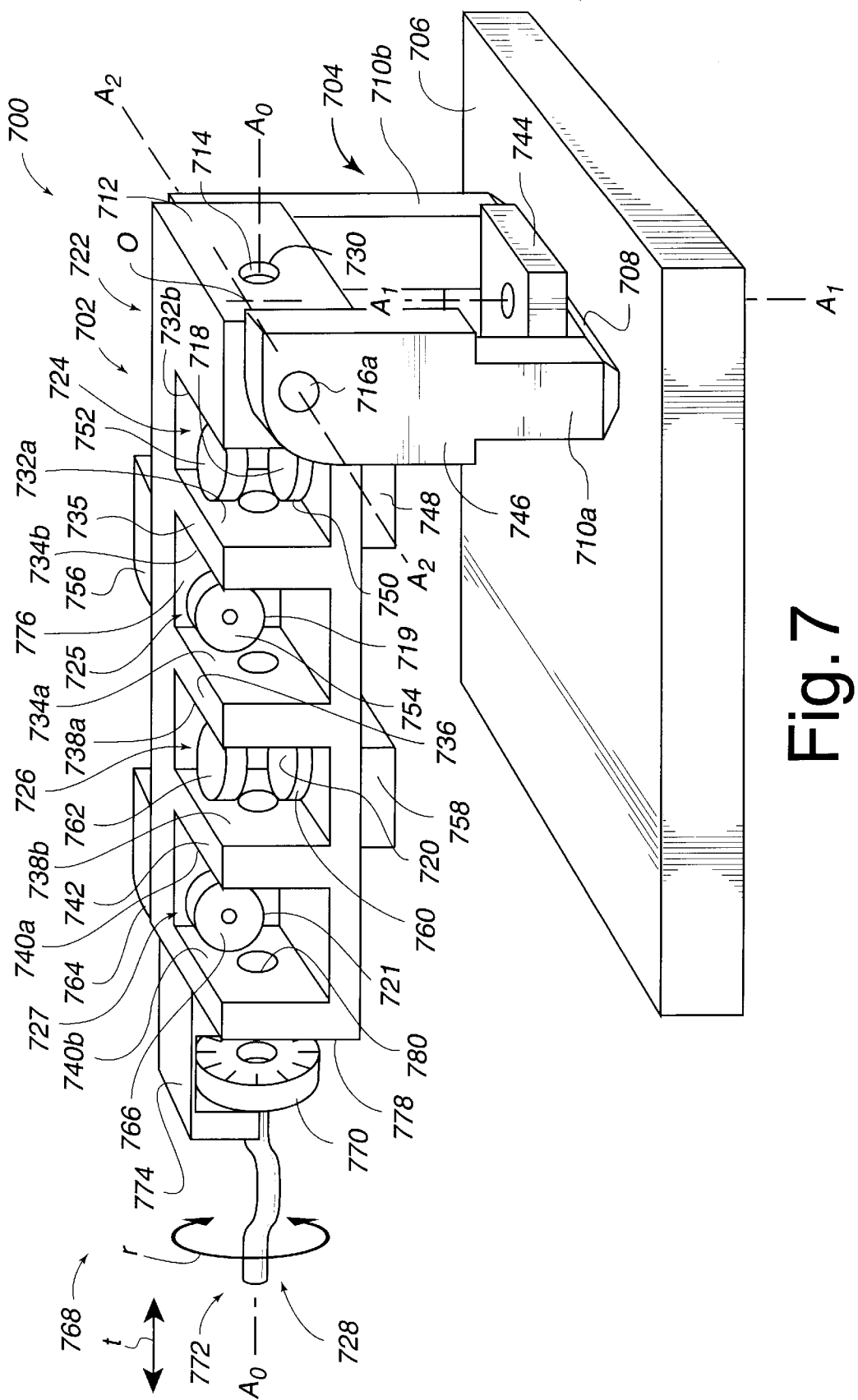
FIG. 7 is an illustration of an apparatus of the invention mounted on a gimbal mechanism.

In another preferred embodiment, the object receiving portion is part of a gimbal apparatus as shown at 700 in FIG. 7. In the perspective view of FIG. 7, the gimbal apparatus 700 of the present invention is illustrated in some detail. The gimbal apparatus 700 preferably includes object receiving portion 702, a U-shaped base portion 704 and a support 706. The U-shaped base portion is rotatably coupled to the support and includes a base 708 and a pair of substantially parallel legs 710a and 710b extending upwardly therefrom that are capable of rotation about axis $A_1$. As used herein, "substantially parallel" will mean that two objects or axis are exactly or almost parallel, i.e., the legs are at least within five or ten degrees of parallel, and are preferably within less than one degree of parallel. Similarly, the term "substantially perpendicular" will mean that two objects or axes are exactly or almost perpendicular, i.e., the legs are at least within five degrees or ten degrees of perpendicular, and, more preferably, within less than one degree of perpendicular.

The elongated flexible object receiving portion 702 is provided with object inlet portion 712 which object inlet portion includes an aperture 714 extending entirely through the object receiving portion. The aperture 714 defines an object axis $A_0$ for an elongated flexible object, such as the shaft portion 118 of the catheter 108 of FIG. 1. The object inlet portion 712 is at least partially disposed between the legs 710a and 710b of the U-shaped base portion, and is pivotally coupled thereto such as by a pair of pivots, one of which is shown as pivot 716a in leg 710a, which pivot lies on axis $A_2$ Another pivot 716b (not shown) is provided in leg 710b. Axes $A_1$ and $A_2$ are substantially mutually perpendicular and intersect at an origin point O within object inlet portion 712. Axis $A_0$ also intersects this origin O and is substantially perpendicular to axes $A_1$ and $A_2$.

The object receiving portion 702 also includes a actuator interface 718 and a translation interface 719. In some preferred embodiments, a second actuator interface 720 and a second translation interface 721 may be included as shown. The object receiving portion 702 includes a bearing section 722, an actuator section 724, a translation sensor section 725, and optionally a second actuator section 726 and translation section 727 as shown. The object receiving portion also includes rotation sensor section 728. The bearing section 722 includes a mass of material provided with a cylindrical bore 730 forming a portion of the aperture 714. The actuator sensor section 724 includes a pair of opposing wall surfaces 732a and 732b, each of which is provided with a cylindrical bore receptive to the cylindrical object and forming a part of the aperture 714 which extends through the object receiving portion. The translation sensor section 725 includes a pair of opposing wall surfaces 734a and 734b of a wall and which are provided with cylindrical bores receptive to the elongated flexible object and therefore also forming a part of the aperture 714. Optional second actuator sensor section 726 and translation section 727 include opposite facing walls 738a and 738b and 740a and 740b, respectively, which walls are analogous to the walls of actuator sensor section 724 and translation sensor section 725 just described. In consequence, when an elongated flexible object is inserted into the object inlet portion 712 along axis $A_0$ it engages the bore 730 of the bearing section 722, and extends through bores provided in the surfaces 732a, 732b, 734a, and 734b (and, optionally, surfaces 738a, 738b, 740a and 740b) to extend completely through the object receiving portion 702 along the aperture 714. In another embodiment of the present invention, walls 735, 746 and 742 are (and therefore their associated wall surfaces) are eliminated, either singly or in combination, as being superfluous.

The object receiving portion 702 is preferably a unitary mass of material made from aluminum or some other lightweight material such as a plastic, preferably cast, molded, and/or machined as a monoblock member having the aforementioned bearing section, translation sensory section, and rotation sensory sections. The materials and construction of U-shaped base portion 704 preferably match the materials and construction techniques used for the production of object receiving portion 702.

The gimbal apparatus 700 illustrated in FIG. 7 constrains an object that is engaged with the object receiving portion 702 to four degrees of freedom. This is accomplished by allowing the U-shaped base portion 704 to rotate around an axis $A_1$ relative to the support 706, by allowing the object receiving portion 702 to rotate around an axis $A_2$ relative to the U-shaped base portion 704, by allowing the object to translate as illustrated by the bi-directional arrow "t" along axis $A_0$ of aperture 714, and by allowing the object to rotate as indicated by arrow "r" around the axis $A_0$ of aperture 714.

Depending on whether one or two actuator/translation sensor pairs are used, as few as four and as many as six electromechanical actuators and transducers are used in association with these four degrees of freedom. More particularly, a first degree of freedom electromechanical transducer 744 is coupled between the U-shaped base portion 708 and the support 706, a second degree of freedom electromechanical transducer 746 is coupled between leg 710a of U-shaped base portion 708 and the object inlet portion 712, a third degree of freedom electromechanical actuator 748, including lower interface 750 and upper interface 752, is coupled between the object receiving portion 702 and an object engaged with the object receiving portion 702, a third degree of freedom electromechanical transducer wheel 754 and sensor 756 is also coupled between the object receiving portion 702 and an object engaged with the object receiving portion 702. Optionally, a second third degree of freedom actuator 758, including upper and lower interfaces 760 and 762 respectively, and a second third degree of freedom transducer wheel 764 and sensor 766 can be coupled as just described for actuator 748 and translation transducer 756. A fourth degree of freedom transducer 768, including disk 770, hollow shaft 772 and sensor 774 as described above, is engaged between the object receiving portion 702 and an object engaged with the object receiving portion 702.

There a number of ways of attaching the actuators and transducers to the various members of the gimbal apparatus 700. In this preferred embodiment, a housing of transducer 744 is attached to the U-shaped base portion 704, and a shaft of the transducer extends through an oversize bore (not shown) in base 708 to engage a press-fit bore (also not shown) in support 706. Therefore, rotation of the U-shaped base portion 704 around axis $A_1$ will cause a rotation of a shaft of transducer 744. A housing of transducer 746 is attached to leg 710a of the U-shaped base portion 704 such that its shaft forms pivot 716a. Therefore, rotation of the object receiving portion 702 around axis $A_2$ will cause a rotation of the shaft of a second transducer 746. Actuator sensor 748 is attached to a wall of actuator section 724, and a shaft of the actuator extends through a bore in the wall to connect lower interface 750 to the actuator sensor. Upper interface 752 is fixedly attached to a wall of actuator section 748. The transducer 756 is attached to object receiving portion 702 and extends through a bore (not shown) in a wall 776 of the translation sensor section 725. The shaft of wheel 754 provides the axis for the translation interface 719 and rotates with the rotation of the translation interface 719. Optional actuator section 726 and translation section 727 are constructed analogously. Disk 770 is rotatable coupled to a wall 778 of rotation sensor section 768 and extends through a bore 780 in wall 778. A photodetector 774 is attached to wall 778 and engages a circumferential surface of disk 770 to sense the rotation thereof.

With reference to all of the Figures, and with particular reference to FIGS. 1 and 7, the shaft 118 of a catheter 108 is inserted into aperture 714 along axis $A_0$, causing the shaft 118 to frictionally engage the actuator interface 718 and the translation interface (wheel) 719. In this instance, the translational interface 719 is a friction wheel made out of a rubber-like material. The shaft 118 is also in engagement with the rotation interface 768 and extends through hollow shaft 772. Rotation of the shaft 118 around the axis $A_0$ as illustrated by the arrow "r" will cause a rotation of disk 770 which is registered on sensor 774. A translation of the shaft 118 along axis $A_0$, however, will not be affected appreciably by hollow shaft 772 or disk 770, but will cause a rotation of the friction wheel 754 which rotates the shaft of the transducer 756. A movement up or down of the catheter 108 will cause a rotation of the shaft (pivot) 716a of transducer 746, and a side-to-side pivoting of the catheter 108 will cause a rotational about axis $A_1$ which is detected by transducer 744.

In an embodiment wherein catheter 108 is an "epidural" instrument, the translational and rotational movements of the catheter will be tracked as just described, except that the translation section 727 and actuator section 726 will be used. The translational motion of the "needle" will be handled by translation section 725 and actuator 724 as described above for the case wherein a catheter is inserted through aperture 714.

To this point, the majority of the discussion has been under the assumption that the transducers are input transducers, i.e., the human/computer interface device is used an input device to the computer 106. However, it is also been mentioned that the interface device 102 can serve as an output device for the computer 106. When used as an output device, output transducers ("actuators") are used to respond to electrical signals developed by the computer 106 to impart a force upon the shaft 118 of catheter 108. This can provide useful movement and force (haptic) feedback to the doctor/trainee or other user. For example, if the catheter encounters a heavily occluded vessel in the "virtual" patient, a force can be generated by actuator 748 making it harder for the doctor/trainee to push the shaft 118 further into the gimbal apparatus 700. Likewise, twisting motions can be imparted on the shaft 118 when the shaft encounters an obstacle within the virtual patient.

It should be noted that force applied to the shaft may not result in any movement of the shaft. This is because the shaft may be inhibited from movement by the hand of the operator who is grasping a handle or grip portion of the shaft. However, the force applied to the shaft may be sensed by the operator as haptic feedback.

With reference to FIG. 7, a method for mechanically interfacing an elongated mechanical object with an electrical system in accordance with the present invention includes first step of defining an origin in 3-dimensional space. This corresponds to the origin O at the intersection of axes $A_1$ and $A_2$. A second step is to physically constrain an elongated object in the 3-dimensional space such that a portion of the object always intersects the origin O and such that a portion of the object extending from the origin O defines a radius in a spherical coordinate system. The elongated object (such as shaft 118 of catheter 108) is physically constrained in a 3-dimensional space by the aperture 714 of the object receiving portion 702. The portion of the shaft 118 extending from origin O defines the radius. A third step includes transducing a first electrical signal related to a first angular coordinate of the radius with a first transducer. This corresponds to the operation of transducer 744 which transduces a first electrical signal related to a first angular coordinate of the radius. A fourth step is transducing a second electrical signal related to a second angular coordinate of the radius. This corresponds to the operation of transducer 746 which transduces a second electrical signal. A fifth step is to transduce a third electrical signal related to the length of the radius, which corresponds to the operation of transducers 756 and/or 762. A sixth and final step is to electrically couple the transducers to an electrical system which, in this instance, is preferably a computer 106. An additional step transduces a fourth electrical signal related to a rotation of the object around an object axis which intersects the origin O. This step corresponds to the operation of rotation transducer 768. The transducers can be input transducers, output transducers, or bi-directional transducers.

It will be noted that the electrical system most frequently described in the present invention is a digital processing system or a computer. However, other digital systems, analog systems, and simple electric or electromechanical system can also be utilized with the apparatus and method of the present invention.

It will also be noted that while specific examples of "elongated objects" and "shafts" have been given, these examples are not meant to be limiting. In general, equivalents of "elongated objects", "elongated cylindrical objects", "shafts" and the like, include any object which can be grasped by a human operator to provide an interface between the operator and a computer system. By "grasp", it is meant that operators may releasably engage a grip portion of the object in some fashion, such as by hand, with their fingertips, or even orally in the case of handicapped persons. The "grip" can be a functional grip or handle attached to an elongated portion of the object, or the grip can be a portion of the object itself (i.e., the shaft, wire or catheter), such as a portion of the length of a shaft that can be gripped and/or manipulated by the operator.

It should also be noted that flexible shafts, such as wires or catheters, do not always require three or four degrees of freedom. For example, if a human/computer interface for a catheter insertion virtual reality system is desired, only a translation interface and a rotation interface such as illustrated in FIG. 2 may be required. This is because a catheter can be moved in and out of a virtual patient (as sensed by translation interface 725) and can be twisted or rotated (as sensed by rotation interface 768), but cannot be, in any practical manner, moved up or down or from side-to-side due to the environmental constraints operating on the catheter. In such applications, therefore, it is desirable to have a human/computer interface with only two degrees of freedom. However, in some instances it is preferable to allow two extra degrees of freedom, such as those provided by gimbal apparatus 700, to fix an angle in three dimensions; thereby, creating a more difficult, and realistic, scenario for the operator/trainee.

While this invention has been described in terms of several preferred embodiments, it is contemplated that alternatives, modifications, permutations and equivalents thereof will become apparent to those skilled in the art upon a reading of the specification and study of the drawings. It is therefore intended that the following appended claims include all such alternatives, modifications, permutations and equivalents as fall within the true spirit and scope of the present invention.

What is claimed:

1. A user interface device for interfacing the motion of a user manipulatable object with a computer system, comprising:
   a) a cylindrical user manipulatable object contacted and manipulatable by a user;
   b) a coupling provided between said user manipulatable object and a surface that allows translation of said user manipulatable object with respect to said surface;
   c) at least one sensor coupled to said user manipulatable object that measures said translation of said object, wherein images are displayed by said computer system in coordination with said translation; and
   (d) a brake mechanism applying a frictional resistive force upon said user manipulatable object in response to an electric signal, said brake mechanism applying said frictional resistive force to impede said translation of said user manipulatable object in coordination with said images displayed by said computer system said frictional resistive force being produced by moving a member of said braking mechanism against said cylindrical user manipulatable object and thereby applying a force substantially perpendicular to said translation of said user manipulatable object.

2. A user interface device as recited in claim 1 wherein said brake mechanism includes a solenoid that applies a force upon said user manipulatable object through a frictional pad.

3. A user interface device as recited in claim 1 wherein said user manipulatable object can be moved in two degrees of freedom which include said translational degree of freedom and a rotational degree of freedom.

4. A user interface device as recited in claim 1 further comprising a local microprocessor separate from said computer system, said local microprocessor receiving a sensor signal from said at least one sensor, reporting sensor data based on said sensor signal to said computer systems and controlling said braking mechanism based on commands sent to said local microprocessor from said computer system.

5. A user interface device as recited in claim 1 wherein said cylindrical user manipulatable object is an elongated flexible object.

6. A user interface device as recited in claim 1 wherein said user manipulatable object is at least a portion of a medical instrument.

7. A user interface device as recited in claim 6 wherein said portion of a medical instrument is a portion of a catheter.

8. A user input device for interfacing the motion of a user manipulatable object with a computer system, comprising:
   a cylindrical user manipulatable object physically contacted and manipulatable by a user;
   a coupling provided between said user manipulatable object and a surface that constrains motion of said user manipulatable object to no more than two degrees of freedom with respect to said surface, said two degrees of freedom including a rotational degree of freedom and a translational degree of freedom;
   at least one sensor coupled to said user manipulatable object that measures the motion of said object in said two degrees of freedom and producing a sensor signal, wherein data based on said sensor signal is reported to said computer system to update a displayed simulation provided by said computer system; and
   a brake mechanism applying a frictional resistive force upon said user manipulatable object in said translational degree of freedom in response to an electric signal, said brake mechanism applying said frictional resistive force to impede the motion of said user manipulatable object in said translational degree of freedom in coordination with simulated images displayed by said computer system, said frictional resistive force being produced by applying a force to said user manipulatable object substantially perpendicular to said translational degree of freedom using said brake mechanism.

9. A user input device as recited in claim 8 wherein said brake mechanism includes a solenoid.

10. A user input device as recited in claim 9 wherein said solenoid applies a force upon said user manipulatable object through a frictional pad coupled to a moving portion of said solenoid.

11. A user input device as recited in claim 8 wherein said force substantially perpendicular to said translational degree of freedom is applied by linearly moving a member of said brake mechanism against said cylindrical user manipulatable object.

12. A user input device as recited in claim 8 wherein said user manipulatable object is at least a portion of a laparoscopic instrument or a catheter.

13. A user interface device for interfacing the motion of a user manipulatable object with a computer system, comprising:
   an elongated user manipulatable object physically contacted and manipulatable by a user;
   a coupling provided between said user manipulatable object and a surface that constrains motion of said user manipulatable object to not more than two degrees of freedom with respect to said surface said two degrees of freedom including a translational degree of freedom and a rotational degree of freedom;
   at least one position sensor coupled to said user manipulatable object that measures the motion of said object in said two degrees of freedom;
   a braking actuator applying a frictional resistive force upon said user manipulatable object in response to an electric signal, said braking actuator applying said frictional resistive force to impede the motion of said user manipulatable object in said translational degree of freedom in coordination with simulated images displayed by said computer system, wherein said frictional resistive force is produced by applying a force to said user manipulatable object substantially perpendicularly to said translational degree of freedom; and a local microprocessor coupled to said position sensor and to said braking actuator, said local microprocessor interfacing said user interface device to said computer system through a communication link and reporting data to said computer system representing signals from said position sensor, wherein said local microprocessor receives commands from said computer system and controls said braking actuator in response to said commands and in parallel with said computer system executing a graphical simulation.

14. A user interface device as recited in claim 13 wherein said braking actuator includes a solenoid.

15. A user interface device as recited in claim 14 wherein said solenoid applies a force upon said user manipulatable object through a frictional pad coupled to a moving portion of said solenoid.

16. A user interface device as recited in claim 13 wherein said elongated user manipulatable object is a cylindrical object.

17. A user interface device as recited in claim 16 wherein said braking mechanism applies said frictional resistive force upon said cylindrical object by engaging said object with a frictional surface.

18. A user interface device as recited in claim 16 wherein said cylindrical object includes at least a portion of a laparoscopic instrument.

19. A user interface device as recited in claim 16 wherein said cylindrical object includes at least a portion of a catheter.

20. A user interface device as recited in claim 13 wherein said at least one position sensor includes two position sensors, wherein one of said position sensors measures motion in said rotational degree of freedom, and another of said position sensors measures motion in said translational degree of freedom.

21. A user interface device as recited in claim 13 wherein said sensor signals reported to said computer system by said local microprocessor are used by said computer system to control the location of a graphical object displayed by said computer system.

22. A user interface device as recited in claim 21 wherein said graphical object displayed by said computer system is a cursor in a graphical interface.

23. A user interface device as recited in claim 13 wherein said sensor is an optical sensor.

* * * * *

UNITED STATES PATENT AND TRADEMARK OFFICE
CERTIFICATE OF CORRECTION

PATENT NO. : 6,215,470 B1
DATED : April 10, 2001
INVENTOR(S) : Rosenberg et al.

It is certified that error appears in the above-identified patent and that said Letters Patent is hereby corrected as shown below:

<u>Title page,</u>
Item [73], correct the Assignee to be:
-- IMMERSION CORPORATION
San Jose, California --

Signed and Sealed this

Eleventh Day of September, 2001

*Attest:*

*Attesting Officer*

NICHOLAS P. GODICI
*Acting Director of the United States Patent and Trademark Office*